(12) United States Patent
Mock-Knoblauch et al.

(10) Patent No.: US 7,696,146 B2
(45) Date of Patent: *Apr. 13, 2010

(54) MIXTURE, COMPRISING A SURFACTANT AND A COSURFACTANT

(75) Inventors: Cordula Mock-Knoblauch, Ludwigshafen (DE); Norbert Wagner, Mutterstadt (DE); Guenter Oetter, Frankenthal (DE); Ludwig Voelkel, Limburgerhof (DE); Susanne Petrovic, Eppelheim (DE); Andreas Fechtenkoetter, Ludwigshafen (DE); Lysander Chrisstoffels, Limburgerhof (DE); Matthias Klueglein, Ludwigshafen (DE); Stefan Becker, Mannheim (DE)

(73) Assignee: BASF SE, Ludwigshafen (DE)

( * ) Notice: Subject to any disclaimer, the term of this patent is extended or adjusted under 35 U.S.C. 154(b) by 394 days.

This patent is subject to a terminal disclaimer.

(21) Appl. No.: 10/556,793

(22) PCT Filed: May 21, 2004

(86) PCT No.: PCT/EP2004/005517

§ 371 (c)(1),
(2), (4) Date: Nov. 15, 2005

(87) PCT Pub. No.: WO2004/104158

PCT Pub. Date: Dec. 2, 2004

(65) Prior Publication Data
US 2007/0041926 A1    Feb. 22, 2007

(30) Foreign Application Priority Data
May 22, 2003  (DE) .............................. 103 23 180

(51) Int. Cl.
*C11D 3/37*    (2006.01)
*C11D 1/00*    (2006.01)

(52) U.S. Cl. ............. 510/475; 510/276; 510/360; 510/361; 510/417; 510/433; 510/434; 510/476; 510/499; 524/486; 524/70.1; 524/70.19

(58) Field of Classification Search ........... 510/276, 510/360, 361, 417, 433, 434, 475, 476, 499; 424/486, 70.1, 70.19

See application file for complete search history.

(56) References Cited

U.S. PATENT DOCUMENTS 6,008,184 A * 12/1999 Pluyter et al. ............... 510/524

(Continued)

FOREIGN PATENT DOCUMENTS

DE    196 34 477    12/1997

(Continued)

OTHER PUBLICATIONS

John Klier et al.: "Properties and Applications of Microemulsions", Adv. Mater., vol. 12, No. 23, pp. 1751-1757, Dec. 1, 2000.

(Continued)

*Primary Examiner*—Brian P Mruk
(74) *Attorney, Agent, or Firm*—Oblon, Spivak, McClelland, Maier & Neustadt, L.L.P.

(57) ABSTRACT

A mixture comprising a surfactant and a cosurfactant is proposed wherein the cosurfactant used is an amphiphilic comb polymer having a backbone with two or more side chains attached to the backbone, where the side chains differ from one another and/or the side chains differ from the backbone in their amphiphilic character.

16 Claims, 1 Drawing Sheet

U.S. PATENT DOCUMENTS 6,677,293 B1 * 1/2004 Allgaier et al. .............. 510/417

FOREIGN PATENT DOCUMENTS

| DE | 198 39 054 |   | 3/2000 |
|----|------------|---|--------|
| DE | 19839054   | * | 3/2000 |
| EP | 0 794 245  |   | 9/1997 |
| GB | 2237813    | * | 5/1991 |

OTHER PUBLICATIONS

Hans-Friedrich Eicke: "Mikroemulsionen- eine wissenschaftliche und anwendungstechnische Fundgrube?", SÖFW-Journal, 118, pp. 311-315, 1992, May 1992 (Not Translated).

* cited by examiner

MIXTURE, COMPRISING A SURFACTANT AND A COSURFACTANT

CROSS REFERENCES TO RELATED APPLICATIONS

This application is a 371 of International Patent Application No. PCT/EP04/05517, filed on May 21, 2004, and claims priority to German Patent Application No. 103 23 180.3, filed on May 22, 2003.

The invention relates to a mixture comprising a surfactant and a cosurfactant, to the use of a mixture for stabilizing emulsions, to a microemulsion comprising a surfactant and a cosurfactant, to the use of a mixture or of a microemulsion, and to detergents, cleaners, disinfectants, wetting agents, coatings, adhesives, leather degreasing compositions, humectants or textile-treatment compositions or pharmaceutical, food, crop protection or cosmetic formulations, in particular sunscreen, skincare or hairstyling compositions, shower gels, shampoos, bath additives or scent oils.

Surfactants are substances which reduce the interfacial tension between liquid phases which are not miscible with one another, a polar phase, often water, and a nonpolar, organic phase, and thus increase their mutual solubility. Surfactants have a characteristic structure and have at least one hydrophilic and one hydrophobic structural unit. This structure is also referred to as amphiphilic.

Surfactants are particularly relevant substances in ecological terms and their environmental compatibility must be ensured. As well as good degradability of surfactant residues in waste waters, it is therefore particularly important to reduce the amounts of surfactant used, as far as possible without impairing their effectiveness, i.e. to increase the efficiency of the surfactants. In this connection, surfactant efficiency is usually used to refer to the amount of surfactant which is required in order to achieve a certain effect, for example in order to solubilize the fraction of nonpolar phase in the polar phase, or vice versa, or in order to reduce to the greatest possible extent the surface tension at the lowest possible concentration.

Customary conventional emulsions can comprise oil and water phases in very different fractions by volume. They have one continuous phase and one disperse phase, which is present as very small spheres which have been stabilized by coating with surfactants, in the continuous phase. Depending on the nature of the continuous phase, the emulsions are described as oil-in-water or water-in-oil. These emulsions are kinetically stable in the ideal case, i.e. they are maintained even for a prolonged period, but not indefinitely. During temperature fluctuations in particular, they may have a tendency toward phase separation as a result of sedimentation, creaming, thickening or flocculation.

So-called microemulsions are thermodynamically stable, fluid, optically clear formulations of two immiscible liquids, such as oil and water. Microemulsions arise when a surfactant, or more frequently a mixture of a surfactant and a cosurfactant, reduces the oil/water interfacial tension to extremely low values, often in the range $10^{-3}$ to $10^{-9}$, preferably $10^{-4}$ to $10^{-6}$, N/m, such that the two insoluble phases remain dispersed by themselves in a homogeneous manner as a result of the thermal agitation. Microemulsions often have bicontinuous structures with equilibrium regions, so-called subphases in the order of magnitude from 100 to 1000 Ångströms (cf. Advanced Materials, 2000, 12, No. 23, pages 1751 et seq.).

Bicontinuous microemulsions comprise two phases, a water phase and an oil phase, in the form of extended adjoining and intertwined domains at whose interface stabilizing interface-active surfactants are concentrated in a monomolecular layer. Bicontinuous microemulsions form very readily, usually spontaneously due to the very low interfacial tension, when the individual components, water, oil and a suitable interface-active system, are mixed. Since the domains have only very small extensions in the order of magnitude of nanometers in at least one dimension, the microemulsions appear visually transparent and are thermodynamically, i.e. indefinitely, stable in a certain temperature range depending on the interface-active system used.

Bicontinuous microemulsions are described, for example, in the article "Mikroemulsionen—eine wissenschaftliche und anwendungstechnische Fundgrube?" [Microemulsions, a scientific and practical treasure trove?] by H.-F. Eicke in SÖFW-Journal 118 (1992), pages 311 to 314.

To achieve the required low interfacial tension at the phase boundaries, the microemulsions comprise special amphiphiles, i.e. interface-active agents, and electrolytes often dissolved in their aqueous phase and optionally further auxiliaries. Electrolytes are primarily added when the amphiphiles are partly or exclusively ionic surfactants.

It is known from DE-A 198 39 054 to increase the efficiency of surfactants by adding additives, the additives used being AB block copolymers with a water-soluble block A and a water-insoluble block B. The blocks A and B can here have molecular weights between 500 and 60 000 g/mol. As block A, preference is given to using a polyethylene oxide block, but generally all water-soluble blocks which form an amphiphile in combination with block B. For block B, polymers of a single monomer or a monomer mixture are described.

However, the described block copolymers have the disadvantage, in particular, that they are obtainable by preparation processes which are suitable for the laboratory scale, but not for industrial-scale use. Said specification refers for the preparation process to DE-A 196 34 477, in which the polymerization using alkali metal organyls is described, i.e. a preparation method unsuitable for industrial-scale use.

It is an object of the present invention to provide substances which can be used as cosurfactants for increasing the efficiency of surfactants in emulsions, in particular in microemulsions, and which can be obtained in an economically advantageous manner on the basis of industrial-scale starting substances and by reaction pathways which can be realized on an industrial scale.

We have found that this object is achieved by a mixture comprising a surfactant and a cosurfactant, wherein the cosurfactant used is an amphiphilic comb polymer having a backbone with two or more side chains attached to the backbone, where the side chains differ from one another and/or the side chains differ from the backbone in their amphiphilic character.

It has surprisingly been found that cosurfactants which have the structure of comb polymers are particularly suitable for the use according to the invention.

DETAILED DESCRIPTION OF THE PREFERRED EMBODIMENTS

Figure 1:
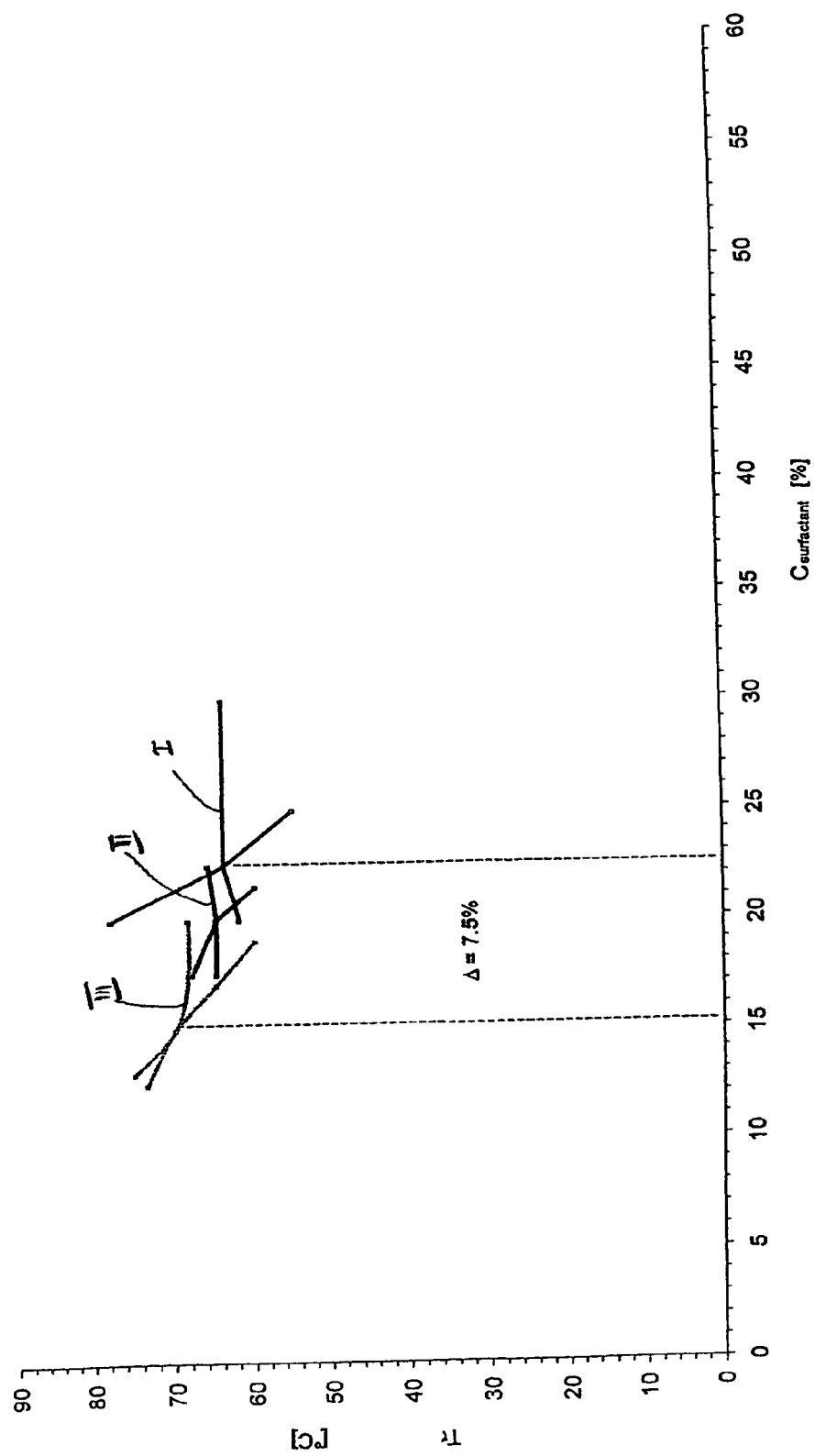
FIG. 1 is a graph showing the results of Application Example 2.

Difference in the amphiphilic character is understood in the present context as meaning that the side chains differ from one another and/or from the backbone with regard to their affinity to polar or to nonpolar phases.

Preferably, the backbone of the comb polymer is hydrophobic and all of the side chains of the comb polymers are hydrophilic. It is particularly favorable if the monomer A present in the backbone itself carries a side chain which preferably differs in its amphiphilic character to the side chains attached to A'.

The comb polymer is preferably formed from repeat structural units $[A]_n$, $[A']_m$ and $[X]_l$, where the structural units
$[A]_n$ and $[A']_m$ form the backbone and the structural unit
$[A']_m$ has an anchor function for binding the side-chain-forming structural units
$[X]_l$ and where the variables n, m and l are mole fractions, where n+m+l=1, n is ≧m and l is >m.

The comb polymer is thus a copolymer where the structural units $[A]_n$ and $[A']_m$ which form the backbone can be arranged arbitrarily, i.e. either strictly alternating (then the variables n and m are equal), or else as block copolymers, as random copolymers or with gradients.

For example, suitable copolymers are those described in EP-A 0 412 389 for use as agents for hydrophobicizing leather or fur hides and are obtainable by free-radical copolymerization of $C_8$ to $C_{40}$-monoolefins with ethylenically unsaturated $C_4$- to $C_8$-dicarboxylic anhydrides by way of bulk polymerization at temperatures of from 80 to 300° C. to give copolymers with molar masses of from 500 to 20 000 g/mol, subsequent solvolysis of the anhydride groups of the copolymers and at least partial neutralization of the carboxyl groups arising during the solvolysis in an aqueous medium with bases.

Preferably, the cosurfactants according to the invention have molecular masses in the range from 500 to 100 000 g/mol, particularly preferably in the range from 1 000 to 50 000 g/mol.

Preferably, the mole fractions n, m and l are, independently of one another, are from 0.001 to 99.9%, preferably n is greater than or equal to m and l is greater than m. Particularly preferably, m is between 0.001 and 0.4, n is between 0.001 and 0.99 and n is between 0.2 and 0.99.

Advantageously, for the formation of the structural unit $[A]_n$, monomers can be used which carry one or more hydrophobic side chains.

Advantageously, the monomer forming the structural unit $[A]_n$ is a substance or a mixture of substances chosen from the list below:
  unbranched or branched alkenes having 15 to 50, preferably having 20 to 35, carbon atoms per molecule, preferably α-olefins,
  ethylene
  reactive polyisobutenes, formed from polyisobutene chains, which also have a reactive double bond at the end or in the vicinity of the end of the polyisobutene chain,
  hydrophobic vinyl or vinylidene compounds, in particular styrene, or
  (meth)acrylates with hydrophobic side chains.

For the formation of the structural unit $[A]_n$, it may thus be advantageous to start from long-chain α-olefins. Also particularly advantageous is the use of reactive polyisobutenes, i.e. of polyisobutenes which are formed from chains which also have a reactive double bond at the end or in the vicinity of the end of the chain.

All of the substances or mixtures of substances listed above are industrial-scale products, and accordingly available at low cost.

To form the structural unit $[A']_m$, i.e. the structural unit which has an anchor function for the binding of side chains, use is preferably made of a substance or a mixture of substances chosen from the list below:
  maleic anhydride or its derivatives, which preferably carry a polymerizable or alkoxylatable side chain,
  vinyl alcohols or their derivatives which preferably carry a polymerizable or alkoxylatable side chain,
  (meth)acrolein or
  (meth)acrylic acid or its derivatives, which preferably carry one or more polymerizable or alkoxylatable side chains.

In the present context, the term "polymerization" or "polymerizable" should be understood as meaning all processes by which a polymeric compound can be prepared. As well as the classic polymerization processes, processes such as polycondensation, polyaddition, in particular, are also intended to be included.

These too are, without exception, also industrial-scale products, and are thus available at low cost.

The monomer forming the structural unit $[X]_l$ is advantageously ethylene oxide or a mixture of ethylene oxide and propylene oxide, which is further reacted, for forming the side chains (n), to give a hydrophilic polyethylene oxide or polyethylene oxide/polypropylene oxide block.

It is particularly favorable to construct the structural unit $[X]_l$ from a mixture of ethylene oxide and propylene oxide, preferably with a propylene oxide content of from 5 to 20%.

It has been found that, for increasing the efficiency of surfactants, particularly effective cosurfactant structures are obtained if the hydrophilic side chains formed from ethylene oxide or ethylene oxide/propylene oxide mixtures are terminally capped with hydrophobic blocks, i.e. all or some of the side chains formed from the hydrophilic ethylene oxide or ethylene oxide/propylene oxide blocks in each case end in a hydrophobic block, preferably a hydrophobic polyalkylene oxide or oligoalkylene oxide or in a branched or unbranched $C_{10}$- to $C_{30}$-alkyl chain.

The structural units $[X]_1$ forming the side chains can also be formed from an unbranched or branched alkyl, cycloalkyl, aryl or aralkyl radical having 4 to 400 carbon atoms or a polyolefin or hydrophobic polyalkylene or oligoalkylene oxide block.

The polyolefin block can preferably be formed from one or more of the following monomers: ethene, propene, 1-butene, 2,3-butene, 2-methyl-1,2-propene (isobutene), 1-pentene, 2,3-pentene, 2-methyl-1,2-butene, 3-methyl-1,2-butene, 2,3-hexene, 3,4-hexene, 2-methyl-1,2-pentene, 2-ethyl-1,2-butene, 3-methyl-1,2-pentene, decene, 4-methyl-1,2-pentene, styrene or from a mixture of olefins of industrially available raffinate streams.

Particularly preference is given to a mixture comprising a cosurfactant, where the monomer forming the structural unit $[A']_m$ is maleic anhydride and the monomer forming the structural unit $[X]_l$ is ethylene oxide. A further preferred mixture comprises a cosurfactant, where the monomer which forms the structural unit $[A']_m$ is maleimide and the side chain(s) is (are) unbranched or branched alkyl radicals having 3 to 20 carbon atoms or a polyethylene oxide or polyethylene oxide/ polypropylene oxide block, which preferably end in a hydrophobic block, in particular a branched or unbranched $C_{10}$- to $C_{30}$-alkyl chain.

Preference is also given to a mixture comprising a cosurfactant, where the monomer forming the structural unit $[A']_m$ is vinyl alcohol, and the monomer X is (meth)acrylic acid or ethylene oxide or a mixture of ethylene oxide and propylene oxide.

Further preferred as the monomer forming the structural unit $[A']_m$ is a vinyl alcohol derivative with a polymerizable side chain and the monomer forming the structural unit $[X]_l$ is vinylpyrrolidone, (meth)acrylic acid or vinyl alcohol.

It is not necessary for all of the structural units A' with anchor function to also be actually functionalized with a side chain in each case. The invention equally also encompasses comb polymers which still contain free anchor groups, where the anchor groups have either not been reacted or have been protected before the reaction. It is thus possible, through corresponding functionalization of just some of the structural units A' with anchor function, to synthesize a polymer with a density of side chains suitable for the specific application case.

When the monomer forming the structural unit $[A']_m$ is maleic anhydride, the maleic anhydride units which do not carry a side chain may be in the form of the anhydride, the monoester or diester, the amide or imide, in the form of the free acid, and in partially or completely neutralized form.

When the monomer forming the structural unit $[A']_m$ is vinyl alcohol, the vinyl alcohol groups which do not carry any side chains may be in the form of the free alcohol or in the form of vinyl acetate.

If the monomer forming the structural unit $[A']_m$ is (meth)acrylate, the nonfunctionalized (meth)acrylate units may be in the form of the ester, amide, free acid, and in partially or completely neutralized form.

As well as the cosurfactants described above, the mixture according to the invention comprises a surfactant. This may also be a mixture of surfactants. In principle, any surfactant from any of the known surfactant groups, in particular ionic or nonionic surfactants, and also mixtures of ionic or nonionic surfactants, can be used.

Depending on the field of use of the mixtures according to the invention, suitable surfactants are, for example, all classical cleaning surfactants, or food-approved surfactants, such as Tweens® or Spans®. As far as the surfactant classes are concerned, nonionic, anionic, cationic, amphoteric surfactants are suitable; in particular also polymer surfactants, peptide surfactants, silicone surfactants, amino acid-based surfactants, sugar surfactants, fat-based surfactants, gemini surfactants, amine oxides, amidoamine oxides, alkylbetaines, ether carboxylates, amphoacetates, alkyl sulfates or sulfosuccinates.

The proportion of the cosurfactant, based on the surfactant, is preferably in the range from 0.01 to 99.99%, in particular between 1 and 50%, particularly preferably between 5 and 25%.

Suitable anionic surfactants are, for example, fatty alcohol sulfates of fatty alcohols having 8 to 22, preferably 10 to 18, carbon atoms, for example $C_9$- to $C_{11}$-alcohol sulfates, $C_{12}$- to $C_{13}$-alcohol sulfates, cetyl sulfate, myristyl sulfate, palmityl sulfate, stearyl sulfate and tallow fatty alcohol sulfate.

Further suitable anionic surfactants are sulfated ethoxylated $C_8$- to $C_{22}$-alcohols (alkyl ether sulfates) or soluble salts thereof. Compounds of this type are prepared, for example, by firstly alkoxylating a $C_8$- to $C_{22}$-, preferably a $C_{10}$- to $C_{18}$-, alcohol, for example a fatty alcohol, and then sulfating the alkoxylation product. For the alkoxylation, preference is given to using ethylene oxide, employing 2 to 50, preferably 3 to 20, mol of ethylene oxide per mole of fatty alcohol. The alkoxylation of the alcohols can, however, also be carried out with propylene oxide on its own and optionally butylene oxide. Also suitable are those alkoxylated $C_8$- to $C_{22}$-alcohols which comprise ethylene oxide and propylene oxide or ethylene oxide and butylene oxide. The alkoxylated $C_8$- or to $C_{22}$-alcohols can contain the ethylene oxide, propylene oxide and butylene oxide units in the form of blocks or in random distribution.

Also suitable are alkanesulfonates, such as $C_8$- to $C_{24}$-, preferably $C_{10}$- to $C_{18}$-, alkanesulfonates, and soaps, such as Na or K salts of $C_8$- to $C_{24}$-carboxylic acids.

Further suitable anionic surfactants are N-acylsarcosinates with aliphatic saturated or unsaturated $C_8$- to $C_{25}$-acyl radicals, preferably $C_{10}$- to $C_{20}$-acyl radicals, for example N-oleoylsarcosinate.

In addition, the mixtures according to the invention can comprise $C_{10}$- to $C_{13}$-linear and/or slightly branched alkylbenzenesulfonates (LAS).

The anionic surfactants are added to the mixture, preferably in the form of salts. Suitable cations in these salts are alkali metal salts, such as sodium, potassium and lithium and ammonium salts, such as, for example, hydroxyethylammonium, di(hydroxyethyl)ammonium and tri(hydroxyethyl)ammonium salts.

Suitable nonionic surfactants are, in particular:

alkoxylated $C_8$- to $C_{22}$-alcohols such as fatty alcohol alkoxylates or oxo alcohol alkoxylates. These may be alkoxylated with ethylene oxide, propylene oxide and/or butylene oxide. Surfactants which may be used here are all alkoxylated alcohols which contain at least two added molecules of one of the alkylene oxides specified above. In this connection, block polymers of ethylene oxide, propylene oxide and/or butylene oxide are suitable, or addition products which contain said alkylene oxides in random distribution. The nonionic surfactants contain, per mole of alcohol, generally 2 to 50, preferably 3 to 20, mol of at least one alkylene oxide. These preferably contain ethylene oxide as alkylene oxide. The alcohols preferably have 10 to 18 carbon atoms. Depending on the nature of the alkoxylation catalyst used in the preparation, the alkoxylates have a broad or narrow alkylene oxide homolog distribution;

alkylphenol alkoxylates, such as alkylphenol ethoxylates with $C_6$- to $C_{14}$-alkyl chains and 5 to 30 alkylene oxide units;

alkyl polyglucosides having 8 to 22, preferably 10 to 18, carbon atoms in the alkyl chain and generally 1 to 20, preferably 1.1 to 5, glucoside units sorbitan alkoxides, also alkoxylated;

N-alkylglucamides, fatty acid alkoxylates, fatty amine alkoxylates, fatty acid amide alkoxylates, fatty acid alkanolamide alkoxylates, alkoxylated, block copolymers of ethylene oxide, propylene oxide and/or butylene oxide, polyisobutene ethoxylates, polyisobutene-maleic anhydride derivatives, monoglycerides and bisglycerides, also alkoxylated.

Particularly suitable nonionic surfactants are alkyl alkoxylates or mixtures of alkyl alkoxylates, as are described, for example, in DE-A 102 43 363, DE-A 102 43 361, DE-A 102 43 360, DE-A 102 43 365, DE-A 102 43 366, DE-A 102 43 362 or in DE-A 43 25 237. These are alkoxylation products which have been obtained by reacting alkanols with alkylene oxides in the presence of alkoxylation catalysts, or are mixtures of alkoxylation products. Particularly suitable starter alcohols are the so-called Guerbet alcohols, in particular ethylhexanol, propylheptanol and butyloctanol. Particular preference is given to propylheptanol. Preferred alkylene oxides are propylene oxide and ethylene oxide, with alkyl alkoxylates with a direct bond of a preferably short polypropylene oxide block to the starter alcohol, as are described, for example, in DE-A 102 43 365, being preferred in particular on the basis of their low residual alcohol content and their good biodegradability.

Alkoxylation catalysts which may be used are bases, for example alkali metal hydroxides or alkali metal alkoxides, but also Lewis acids, for example $BF_3$, $SbCl_5$, $SnCl_4.2H_2O$, $BF_3.H_3BO_4$, or $BF_3$ dietherate. Particularly suitable alkoxylation catalysts are double hydroxide clays, such as hydrotalcite, which may, in particular, be modified with additives, as described in DE-A 43 25 237.

Depending on the choice of alkoxylation catalyst, specific properties of the alkoxylates result in each case, in particular with regard to the distribution of the degree of alkoxylation. For example, if the last-mentioned double-hydroxide clays are used, the alkoxylation products obtained have a narrow molecular weight distribution or homolog distribution and are particularly suitable for use in the mixtures according to the invention with cosurfactants.

The advantageous properties described above, in particular with regard to the degree of alkoxylation, are also achieved through the use of double metal cyanide (DMC) compounds, as are described, for example, in DE-A 102 43 361 as alkoxylation catalysts The invention also provides for the use of a mixture comprising a surfactant and an above-described cosurfactant with the structure of an amphiphilic comb polymers for stabilizing emulsions, in particular microemulsions. In the present context, stabilization means that the efficiency of surfactants is increased through the addition of cosurfactants, i.e. the solubilization of a defined oil/water mixture is made possible under defined conditions with a relatively small amount of surfactant.

The above-described cosurfactants with the structure of amphiphilic comb polymers are particularly preferably suitable for stabilizing microemulsions, i.e. for shifting the so-called X point, which represents the lowest concentration of surfactant at a given temperature from which the thermodynamic state of the microemulsion, i.e. the single-phase state when examined microscopically, arises.

The mixtures according to the invention can in principle be used in all areas where emulsions play a role, for example in the fields of application listed in DE-A 101 18 480 for mixtures comprising a surfactant and an AB block copolymer as additive (cosurfactant), which also comprise additives whose efficiency can be increased by the surfactant/additive system: for example as crop restoration, growth or crop protection compositions, products with microbiocidal active ingredients, products with positively or negatively acting microorganisms, in particular with a content of enzymes, cleaners and/or care compositions for the home and for commercial purposes, disinfectants, hair, bodycare or cleansing compositions, automobile cleaning, care and/or preservation compositions, textile treatment compositions, leather and/or fur care compositions, as paints, coatings, medicaments, construction aids, toothpastes or mouthwashes.

Synergistic effects, as are described in DE-A 101 18 480 for the surfactant/AB block copolymer system in combination with additional biocides, microorganisms and/or any other active ingredients, are achieved correspondingly for systems comprising the mixtures according to the invention comprising a surfactant and a cosurfactant, and corresponding additives, in particular biocides, microorganisms and/or any other active ingredients.

The invention also further provides a microemulsion comprising a surfactant and a cosurfactant, where the cosurfactant used is a substance or a mixture of substances with the structure of an amphiphilic comb polymer, as described above. These may be bicontinuous microemulsions, although non-bicontinuous microemulsions are equally encompassed by the invention.

The mixtures according to the invention are optimally suitable for the uptake and release of hydrophobic substances, in particular the use as detergent, emulsifier, foam regulator, wetting agent for hard surfaces or as reaction medium for organic, inorganic, bioorganic or photochemical reactions.

Preference is given to use in detergents, surfactant formulations for the cleaning of hard surfaces, humectants, cosmetic, pharmaceutical and crop protection formulations, paints, coating, adhesives, leather-degreasing compositions, formulations for the textile industry, fiber processing, metal processing, food industry, water treatment, paper industry, fermentation, mineral processing, fire protection or in emulsion polymerizations.

The invention further provides detergents, cleaners, disinfectants, wetting agents, coatings, adhesives, leather degreasing compositions, humectants or textile treatment compositions pharmaceutical, food, crop protection or cosmetic formulation, in particular sunscreen, skincare or hairstyling compositions, shower gels, shampoos, bath additives or scent oils comprising, as well as customary ingredients, a mixture comprising a surfactant and a cosurfactant as described above or a microemulsion comprising a surfactant and a cosurfactant.

The invention is described in more detail below by reference to examples.

Preparation Examples 1 to 3

In a polymerization reactor made of steel and fitted with stirrer and metering devices, 1195 g of a $C_{20}$-$C_{24}$-$\alpha$-olefin mixture were initially introduced and heated to 190° C. with stirring in a gentle stream of nitrogen. As soon as this temperature had been reached, 392 g of maleic anhydride heated to 70° C. and, separately from this, 16 g of di-tert-butyl peroxide were added uniformly over the course of 4 hours. This is thus a free-radical polymerization for the preparation of the backbone of an exemplary comb polymer. The reaction mixture was then stirred for two hours at 190° C. and then esterified to connect the side chains.

For this, an alkyl polyglycol ether of a $C_{18}$-oxo alcohol with ethylene oxide blocks of the following length and in the amount given in each case:

Example 1 11 EO units, 1450 g,

Example 2 25 EO units, 2665 g and

Example 3 80 EO units, 6878 g, was introduced at 150° C. with stirring and the mixture was stirred for five hours. Subsequently, the reaction mixture was cooled to 90° C. with stirring. Over the course of half an hour, 160 g of a 50% strength aqueous sodium hydroxide solution and enough water, heated to 90° C., to give a solution with a solids content of 30% were then each added separately from one another. The reaction mixture was stirred for 4 hours in the temperature range from 90 to 95° C. and then cooled to ambient temperature. This gave a slightly viscous aqueous dispersion of a copolymer in which 50 mol % of the carboxyl group formed overall were neutralized.

APPLICATION EXAMPLES

The FIGURE which follows shows the shift in the X point, i.e. the minimum concentration of surfactant at a given temperature below which, for the reference system water/n-decane and a given surfactant (Lutensol® ON 50 from BASF AG), the water phase and the n-decane phase are completely miscible and a stable microemulsion arises, with addition of the following cosurfactants:

Application Example 1

Copolymer of maleic anhydride and $C_{20}$-$C_{24}$-α-olefin in which half of the maleic anhydride subunits have been esterified with Pluriol® A 750 I from BASF AG, i.e. a methyl polyethylene glycol with an average molecular mass of 750 g/mol.

Application Example 2

Copolymer of maleic anhydride and $C_{20}$-$C_{24}$-α-olefin in which half of the maleic anhydride subunits have been esterified with Lutensol® AT 11 from BASF AG, i.e. a $C_{16}$-$C_{18}$-fatty alcohol ethoxylate with 11 ethylene oxide units.

Each of the cosurfactants was added in each case in an amount of 10% by weight to the surfactant Lutensol® ON 50 from BASF AG, i.e. a $C_{10}$-oxo alcohol ethoxylate with 5 ethylene oxide units.

In the case of the comparative example without cosurfactant, the X point was at 22.5% Lutensol® ON 50 at 64° C., in Application example 1, with the addition of cosurfactant, at 20% Lutensol® ON 50, at 65° C. and in Application example 2, with the addition of cosurfactant, at 15% Lutensol® ON 50, at 70° C.

In the attached FIGURE, the concentration of the surfactant Lutensol® ON 50, $c_{Surfactant}$ in the fig, is shown on the abscissa in % by weight, and the temperature is shown on the ordinate in ° C. Sections from the respective phase diagrams are given for the system water/n-decane 1:1 and the abovementioned surfactant under I for comparison, i.e. without the addition of a cosurfactant, under II for Application example 1 according to the invention and under III for Application example 2 according to the invention. The diagram clearly shows the shift in the X point in the application examples according to the invention (representation in II and III) compared with the prior art (representation I).

We claim:

1. A microemulsion, comprising a surfactant and a cosurfactant, wherein said cosurfactant is a mixture,
    wherein said mixture comprises a surfactant and a cosurfactant, wherein said cosurfactant is an amphiphilic comb polymer comprising a backbone, wherein at least two side chains are attached to said backbone, and wherein:
    (i) said at least two side chains differ from one another,
    (ii) said at least two side chains differ from the backbone in their amphiphilic character, or
    (iii) said at least two side chains differ from one another and said at least two side chains differ from the backbone in their amphiphilic character,
    wherein said comb polymer comprises repeat structural units
    $[A]_n$, $[A']_m$, and $[X]_l$ where the structural units
$[A]_n$ and $[A']_m$
form the backbone and the structural unit
$[A']_m$
has an anchor function for binding the side-chain-forming structural units
$[X]_l$
and wherein the variables n, m and l are mole fractions where
n+m+l=1,
n≧m and
l>m.

2. The microemulsion as claimed in claim 1, wherein the backbone of the comb polymer is hydrophobic and wherein all side chains of the copolymer are hydrophilic.

3. The microemulsion as claimed in claim 1, wherein the cosurfactant has an average molecular mass in the range from 500 to 100 000 g/mol.

4. The microemulsion as claimed in claim 1, wherein the monomer A comprises at least one hydrophobic side chain.

5. The microemulsion as claimed in claim 1, wherein the monomer forming the structural unit
$[A]_n$
is a substance selected from the group consisting of:
    an unbranched alkene comprising 15 to 50 carbon atoms per molecule,
    a branched alkene comprising 15 to 50 carbon atoms per molecule,
    ethylene,
    a reactive polyisobutene, formed from polyisobutene chains, which also have a reactive double bond at the end or in the vicinity of the end of the polyisobutene chain,
    a hydrophobic vinyl compound,
    hydrophobic vinylidene compound,
    a (meth)acrylate comprising hydrophobic side chains,
    and mixtures thereof.

6. The microemulsion as claimed in claim 1, wherein the monomer forming the structural unit
$[A']_m$
is a substance selected from the group consisting of:
    maleic anhydride,
    a vinyl alcohol,
    (meth)acrolein and
    (meth)acrylic acid.

7. The microemulsion as claimed in claim 1, wherein
$[X]_l$
is a hydrophilic polyethylene oxide or polyethylene oxide/polypropylene oxide block.

8. The microemulsion of claim 7, wherein the monomer forming the structural unit
$[X]_l$
is a mixture of ethylene oxide and propylene oxide.

9. The microemulsion of claim 7, wherein at least one of the side chains formed from the hydrophilic polyethylene oxide or polyethylene oxide/propylene oxide blocks ends in a hydrophobic block or in a branched or unbranched $C_{10}$- to $C_{30}$-alkyl chain.

10. The microemulsion of claim 1, wherein
$[X]_l$
is selected from the group consisting of an unbranched alkyl radical, a branched alkyl radical, a cycloalkyl radical, an aryl radical, an aralkyl radical comprising 4 to 400 carbon atoms, a hydrophobic polyalkylene, and an oligoalkylene oxide block.

11. The microemulsion as claimed in claim 10, wherein the hydrophobic polyalkylene or oligoalkylene oxide block is formed from one or more of the following monomers: propene oxide, 1-butene oxide, 2,3-butene oxide, 2-methyl-1,2-propene oxide (isobutene oxide), 1-pentene oxide, 2,3-pentene oxide, 2-methyl-1,2-butene oxide, 3-methyl-1,2-butene oxide, 2,3-hexene oxide, 3,4-hexene oxide, 2-methyl-1,2-pentene oxide, 2-ethyl-1,2-butene oxide, 3-methyl-1,2-pentene oxide, decene oxide, 4-methyl-1,2-pentene oxide, styrene oxide or from a mixture of oxides of industrially available raffinate streams.

12. The microemulsion of claim 1, wherein the monomer forming the structural unit $[A']_m$ is maleic anhydride and the monomer X is ethylene oxide.

13. The microemulsion of claim 1, wherein the monomer forming the structural unit $[A']_m$ is maleimide and the side chain-forming structural units $[X]_l$ are unbranched or branched alkyl radicals comprising 3 to 20 carbon atoms or polyethylene oxide or polyethylene oxide/polypropylene oxide blocks.

14. The microemulsion of claim 1, wherein the monomer forming the structural unit $[A']_m$ is vinyl alcohol and the monomer X is (meth)acrylic acid or ethylene oxide or a mixture of ethylene oxide and propylene oxide.

15. A microemulsion, comprising a mixture and at least one additional ingredient, wherein said mixture comprises a surfactant and a cosurfactant, wherein said cosurfactant is an amphiphilic comb polymer comprising a backbone, wherein at least two side chains are attached to said backbone, and wherein:

(i) said at least two side chains differ from one another,
(ii) said at least two side chains differ from the backbone in their amphiphilic character, or
(iii) said at least two side chains differ from one another and said at least two side chains differ from the backbone in their amphiphilic character, wherein the comb polymer comprises repeat structural units $[A]_n$, $[A']_m$, and $[x]_l$ where the structural units $[A]_n$ and $[A']_m$ form the backbone and the structural unit $[A']_m$ has an anchor function for binding the side-chain-forming structural units $[X]_l$ and wherein the variables n, m and l are mole fractions where n+m+l=1,
n≧m and
l>m.

16. The microemulsion as claimed in claim 15, wherein the backbone of the comb polymer is hydrophobic and wherein all side chains of the copolymer are hydrophilic.

\* \* \* \* \*